(12) United States Patent
Rao (10) Patent No.: US 7,435,255 B1
(45) Date of Patent: Oct. 14, 2008

(54) DRUG-ELUTING STENT AND METHODS OF MAKING

(75) Inventor: K. T. Venkateswara Rao, San Jose, CA (US)

(73) Assignee: Advnaced Cardiovascular Systems, Inc., Santa Clara, CA (US)

( * ) Notice: Subject to any disclaimer, the term of this patent is extended or adjusted under 35 U.S.C. 154(b) by 196 days.

(21) Appl. No.: 10/668,077

(22) Filed: Sep. 22, 2003

Related U.S. Application Data (63) Continuation-in-part of application No. 10/293,108, filed on Nov. 13, 2002, now Pat. No. 7,144,422.

(51) Int. Cl.
*A61F 2/06* (2006.01)
(52) U.S. Cl. ............. 623/1.42; 623/1.13; 623/1.15
(58) Field of Classification Search ................ 623/1.15, 623/1.12, 1.13, 1.23, 1.39, 1.42, 1.44
See application file for complete search history.

(56) References Cited

U.S. PATENT DOCUMENTS

| | | |
|---|---|---|
| 3,839,743 A | 10/1974 | Schwarcz |
| 4,346,028 A | 8/1982 | Griffith |
| 4,377,030 A | 3/1983 | Pettenpaul et al. |
| 4,417,576 A | 11/1983 | Baran |
| 4,423,725 A | 1/1984 | Baran et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallsten et al. |
| 4,733,665 A | 3/1988 | Palmaz |
| 4,739,762 A | 4/1988 | Palmaz |
| 4,768,507 A | 9/1988 | Fischell et al. |
| 4,776,337 A | 10/1988 | Palmaz |

(Continued)

FOREIGN PATENT DOCUMENTS

DE        36 40 745        6/1987

(Continued)

OTHER PUBLICATIONS

Bull, "Parylene Coating for Medical Applications", Medical Product Manufacturing News, 2 pgs, Mar. 1993.

(Continued)

*Primary Examiner*—Bruce E. Snow
(74) *Attorney, Agent, or Firm*—Squire, Sanders & Dempsey L.L.P.

(57) ABSTRACT

An intravascular stent having a prefabricated, patterned tubular sleeve portion for controlled release of therapeutic drugs and for delivery of the therapeutic drugs in localized drug therapy in a blood vessel is disclosed. The patterned sleeve may be releasably attached to at least a portion of an outer surface of the stent structure. Alternatively, a plurality of individual filament strands are longitudinally arranged around an outer surface of a stent structure in a spaced apart orientation and loaded with at least one therapeutic drug for the release thereof at a treatment site. The stent has a high degree of flexibility in the longitudinal direction, yet has adequate vessel wall coverage and radial strength sufficient to hold open an artery or other body lumen. Methods for making the same are also disclosed.

20 Claims, 8 Drawing Sheets

U.S. PATENT DOCUMENTS

| | | | |
|---|---|---|---|
| 4,816,339 A | 3/1989 | Tu et al. |
| 4,877,030 A | 10/1989 | Beck et al. |
| 4,878,906 A | 11/1989 | Lindemann et al. |
| 4,879,135 A | 11/1989 | Greco et al. |
| 4,902,289 A | 2/1990 | Yannas |
| 4,994,298 A | 2/1991 | Yasuda |
| 5,019,090 A | 5/1991 | Pinchuk |
| 5,059,211 A | 10/1991 | Stack et al. |
| 5,062,829 A | 11/1991 | Pryor et al. |
| 5,064,435 A | 11/1991 | Porter |
| 5,084,065 A | 1/1992 | Weldon et al. |
| 5,085,629 A | 2/1992 | Goldberg et al. |
| 5,100,429 A | 3/1992 | Sinofsky et al. |
| 5,108,370 A | 4/1992 | Walinsky |
| 5,108,755 A | 4/1992 | Daniels et al. |
| 5,123,917 A | 6/1992 | Lee |
| 5,151,105 A | 9/1992 | Kwan-Gett |
| 5,156,623 A | 10/1992 | Hakamatsuka et al. |
| 5,158,548 A | 10/1992 | Lau et al. |
| 5,163,951 A | 11/1992 | Pinchuk et al. |
| 5,163,952 A | 11/1992 | Froix |
| 5,163,958 A | 11/1992 | Pinchuk |
| 5,192,311 A | 3/1993 | King et al. |
| 5,197,977 A | 3/1993 | Hoffman, Jr. et al. |
| 5,199,951 A | 4/1993 | Spears |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,330,500 A | 7/1994 | Song |
| 5,342,348 A | 8/1994 | Kaplan |
| 5,342,621 A | 8/1994 | Eury |
| 5,356,433 A | 10/1994 | Rowland et al. |
| 5,383,928 A | 1/1995 | Scott et al. |
| 5,389,106 A | 2/1995 | Tower |
| 5,411,551 A | 5/1995 | Winston et al. |
| 5,413,597 A | 5/1995 | Krajicek |
| 5,419,760 A | 5/1995 | Narcisco, Jr. |
| 5,421,955 A | 6/1995 | Lau et al. |
| 5,439,446 A | 8/1995 | Barry |
| 5,441,515 A | 8/1995 | Khosravi et al. |
| 5,458,605 A | 10/1995 | Klemm |
| 5,514,154 A | 5/1996 | Lau et al. |
| 5,527,337 A | 6/1996 | Stack et al. |
| 5,578,075 A | 11/1996 | Dayton |
| 5,605,696 A | 2/1997 | Eury et al. |
| 5,700,286 A | 12/1997 | Tartaglia et al. |
| 5,707,385 A * | 1/1998 | Williams ............... 606/192 |
| 5,780,807 A | 7/1998 | Saunders |
| 5,830,217 A | 11/1998 | Ryan |
| 5,843,172 A | 12/1998 | Yan |
| 6,131,266 A | 10/2000 | Saunders |
| 6,146,322 A | 11/2000 | Papirov et al. |
| 6,152,869 A | 11/2000 | Park et al. |
| 6,168,602 B1 | 1/2001 | Ryan |
| 6,254,632 B1 | 7/2001 | Wu et al. |
| 6,261,316 B1 | 7/2001 | Shaolian et al. |
| 6,261,320 B1 | 7/2001 | Tam et al. |
| 6,273,908 B1 | 8/2001 | Ndondo-Lay |
| 6,379,381 B1 | 4/2002 | Hosainy et al. |
| 6,391,033 B2 | 5/2002 | Ryan |
| 6,419,692 B1 | 7/2002 | Yang et al. |
| 6,432,133 B1 | 8/2002 | Lau et al. |
| 6,436,132 B1 | 8/2002 | Patel et al. |
| 6,530,950 B1 | 3/2003 | Alvarado et al. |
| 6,540,776 B2 | 4/2003 | Sanders Millare et al. |
| 6,613,084 B2 | 9/2003 | Yang |
| 6,629,992 B2 | 10/2003 | Bigus et al. |
| 6,629,994 B2 | 10/2003 | Gomez et al. |
| 6,663,665 B2 | 12/2003 | Shaolian et al. |
| 6,899,727 B2 | 5/2005 | Armstrong et al. |
| 6,939,368 B2 | 9/2005 | Simso |
| 2001/0032009 A1 * | 10/2001 | Layne et al. ............... 623/1.13 |
| 2002/0138129 A1 | 9/2002 | Armstrong et al. |
| 2003/0078647 A1 * | 4/2003 | Vallana et al. ............ 623/1.11 |
| 2003/0114919 A1 | 6/2003 | McQuiston et al. |
| 2003/0153901 A1 * | 8/2003 | Herweck et al. ......... 604/891.1 |
| 2003/0166779 A1 | 9/2003 | Khemani et al. |
| 2003/0181973 A1 | 9/2003 | Sahota |
| 2003/0212447 A1 | 11/2003 | Euteneuer et al. |
| 2006/0089705 A1 * | 4/2006 | Ding et al. ................ 623/1.15 |

FOREIGN PATENT DOCUMENTS

| | | |
|---|---|---|
| DE | 44 07 079 | 9/1994 |
| EP | 0 567 788 | 11/1993 |
| EP | 0 604 022 | 1/1994 |
| EP | 0 578 998 | 6/1994 |
| EP | 0 621 017 | 10/1994 |
| EP | 0 623 354 | 11/1994 |
| WO | WO 91/17789 | 11/1991 |
| WO | WO 93/06792 | 4/1993 |
| WO | WO 95/29647 | 11/1995 |

OTHER PUBLICATIONS

Casper et al., "Fiber-Reinforced Absorbable Composite for Orthopedic Surgery", Science and Engineering, vol. 53, pp. 497-501, Fall Meeting 1985.

Hahn et al., "Glow Discharge Polymers as Coatings for Implanted Devices", Univ. of Missouri, pp. 109-113, 1981.

Hahn et al., "Biocompability of Glow-Discharge-Polymerized Films and Vacuum-Deposited Parylene", Applied Polymer Symposium 38, pp. 55-64, 1984.

Kelley et al., "Totally Resorbable High-Strength Composite Material", Advances in Biomedical Polymers, Ed. By Charles G. Gebelein, pp. 75-85, 1987.

Muller et al., "Advances in Coronary Angioplasty: Endovascular Stents", Coronary Artery Disease, vol. 1, No. 4, 10 pgs, 1990.

Nichols et al., "Electrical Insulation of Implantable Devices by Composite Polymer Coatings", Univ. of Missouri, Paper No. 87-0110, pp. 57-62, 1987.

Olson "Parylene, a Biostable Coating for Medical Applications", Nova Tran Parylene Coating Services Jul. 25, 1988 and Nov. 14, 1988 10 pgs.

"Parylene Conformal Coating" by Nova Tran Custom Coating Services, 8 pgs, (undated).

Schatz "A View of Vascular Stents", Arizona Heart Institute Foundation, Phoenix Arizona, 15 pgs, 1988.

Schmidt et al., "Long-Term Implants of Parylene-C Coated Microelectrodes", Medical & Biological Engineering & Computing, pp. 96-101, 1988.

Shing-Chiu Wong et al., "An Update on Coronary Stents", Cardio, Feb. 1992, 8 pgs.

* cited by examiner

DRUG-ELUTING STENT AND METHODS OF MAKING

This application is a continuation-in-part of U.S. Ser. No. 10/293,108 filed Nov. 13, 2002, now U.S. Pat. No. 7,144,422 the entire contents of which are incorporated herein by reference thereto.

BACKGROUND OF THE INVENTION

This invention relates to vascular repair devices, and in particular intravascular stents, which are adapted to be implanted into a patient's body lumen, such as a blood vessel or coronary artery, to maintain the patency thereof. Stents are particularly useful in the treatment of atherosclerotic stenosis in arteries and blood vessels. More particularly, the invention concerns a drug-eluting stent delivery system consisting of an intravascular device having a local drug-eluting component that is capable of eluting therapeutic drugs with uniform and controlled drug distribution at the treatment site while providing the intravascular device with a biocompatible and/or hemocompatible surface.

Intravascular interventional devices such as stents are typically implanted within a vessel in a contracted state, and expanded when in place in the vessel in order to maintain the patency of the vessel to allow fluid flow through the vessel. Stents have a support structure such as a metallic structure to provide the strength required to maintain the patency of the vessel in which it is to be implanted, and are typically provided with an exterior surface coating to provide a biocompatible and/or hemocompatible surface. Since it is often useful to provide localized therapeutic pharmacological treatment of a blood vessel at the location being treated with the stent, it is also desirable to provide intravascular interventional devices such as stents with a biocompatible and/or hemocompatible surface coating of a polymeric material with the capability of being loaded with therapeutic agents, to function together with the intravascular devices for placement and release of the therapeutic drugs at a specific intravascular site.

Drug-eluting stent devices have shown great promise in treating coronary artery disease, specifically in terms of reopening and restoring blood flow in arteries stenosed by atherosclerosis. Restenosis rates after using drug-eluting stents during percutaneous intervention are significantly lower compared to bare metal stenting and balloon angioplasty. However, current design and fabrication methods for drug-eluting stent devices are not optimal. Accordingly, various limitations exist with respect to such current design and fabrication methods for drug-eluting stents.

One significant limitation, for example, is that current designs for drug-eluting stents fail to provide for uniform drug distribution in the artery. Since uniformity is dictated by metal stent skeletal structure, increasing uniformity by increasing the metal stent surface area makes the stent stiff and compromises flexibility and deliverability. Additionally, current device designs incorporate expandable ring elements and connectors, which are then coated using a polymer plus drug coating or loaded with microreservoirs of drug. The expandable nature of the rings limits the extent of uniformity in coverage and drug distribution that can be achieved. Further limitations include the mixture of the drug in a polymer and/or solvent solution which is then spray coated on the entire stent surface with a primer, drug, and topcoat layers being used to control release kinetics. This approach tends to cause cracking in the drug-coating layer since the layer also undergoes stretching during stent expansion, and considerable washout of the drug into the blood stream, and only a fraction gets into the tissue/artery. Further, the amount of the drug that can be loaded on the stent is limited by mechanical properties of the coating, since the higher the drug content in the polymer makes the coating more brittle and causes cracking thereto. Therefore, loading a higher drug dose requires coating with more polymer on the device. Other limitations in current fabrication methods of drug-eluting stents include the necessity of several coating steps along the length of the stent which is time consuming. Special equipment for crimping the drug-eluting stent on the balloon and to securely attach the stent on the balloon is also needed in accordance with current fabrication methods. As conventional spray coating is capable of programming only one drug release rate kinetics, variation of drug dosing and release kinetics along the length of the stent is not possible using the current coating process.

What has been needed and heretofore unavailable is a novel design that decouples the two major functional characteristics of the drug-eluting stent device, namely the purely mechanical stent structure and the local drug-eluting component. Current devices are constrained by their design construct which necessitates optimizing both factors-mechanical stent expansion and drug-elution kinetics simultaneously. Thus, it would be desirable to have a stent structure that is optimally designed for expansion (i.e., allowable stress/strain, scaffolding, radial strength, etc.) independent of the drug-eluting component, and the drug-eluting component designed for local drug release independent of mechanical factors associated with stent expansion. The present invention meets these and other needs.

SUMMARY OF THE INVENTION

The present invention is directed to intraluminal devices, and more particularly, to a drug-eluting stent delivery system for controlled release of therapeutic drugs and for delivery of the therapeutic drugs in localized drug therapy in a blood vessel. In one aspect, the drug-eluting stent delivery system includes a prefabricated patterned tubular sleeve portion having individual drug-loaded elements, the sleeve being releasably attached to an outside surface area of an underlying stent structure in an expanded condition. At least a portion of the patterned sleeve portion decouples or detaches from the outside surface of the stent when the stent is expanded. The independent drug-loaded elements that are loaded into the decoupled sleeve are held against the body lumen wall by the expanded stent pressing on the decoupled sleeve and pushing it into contact with the body lumen wall, such as a coronary artery wall. In another aspect, the drug-eluting stent delivery system includes a plurality of individual filament strands attached in a spaced apart orientation around an outside surface area of the stent and loaded with at least one therapeutic drug for the controlled release thereof at a treatment site. Methods for making different types of a drug-eluting stent delivery system are also disclosed herein.

In one embodiment, the present invention accordingly provides for a drug-eluting stent delivery system for controlled release of therapeutic drugs and for delivery of the therapeutic drugs in localized drug therapy in a blood vessel. A pattern of struts are interconnected to form a structure that expands into the walls of a body lumen to maintain the patency of the vessel. The pattern of struts include a plurality of flexible cylindrical rings being expandable in a radial direction with each of the rings having a first delivery diameter and a second implanted diameter while aligned on a common longitudinal axis. At least one link of the stent is attached between adjacent rings to form the stent. The stent is formed at least in part of a metallic material such as stainless steel, platinum, titanium, tantalum, nickel-titanium, cobalt-chromium or alloys thereof.

A polymeric sleeve, fabricated as a patterned tube, is loaded with at least one therapeutic drug for the release thereof at a treatment site. In one aspect, the polymeric sleeve may be attached to at least a portion of an outside surface area of the stent structure. In another aspect, the polymeric sleeve may be completely detached from the stent and held against the body lumen wall by the underlying stent structure. Various therapeutic drugs that can be used in combination with the polymeric sleeve include antiplatelets, anticoagulants, antifibrins, anti-inflammatories, antithrombins, and antiproliferatives. Several drug-loadable polymers, such as poly(methyl methacrylate) ("PMMA"), poly(ethylene-co-vinyl alcohol) ("EVAL"), poly(butyl methacrylate) ("PBMA"), polyglycolic acid ("PGA"), poly(L-lactic acid) ("PLLA"), copolymers and blends thereof, and nanotubes of carbon, can be used to fabricate the drug-loaded sleeve of the invention. The thickness of the drug-loaded polymeric sleeve ranges from about 0.001 microns to about 100.000 microns. The elastic modulus or stiffness of the polymeric sleeve itself ranges from about 0.05 megapascals to about 30.00 megapascals.

The polymeric sleeve is fabricated from a predesigned pattern having independent drug-loaded elements to achieve a desired local elution profile and therapeutic drug dose in the artery. The predesigned pattern of the polymeric sleeve as a solid tube can be formed by various techniques such as etching or cutting. The drug-loaded polymeric sleeve is prefabricated in a desired dimension by using one of the known polymer processing techniques in the art including extrusion, injection molding, laser cutting, slip casting, and plasma polymerization. As a further mechanism of controlling elution of the therapeutic drug at the treatment site, the polymeric sleeve can be coated with at least one additional layer of polymer material as a barrier layer. The drug loading capacity of the polymeric sleeve portion typically varies with the thickness of the polymer, drug to polymer ratio, drug density, and drug properties.

In use, the drug-loaded polymeric sleeve is decoupled from at least a portion of the outer stent structure upon expansion of the underlying stent and independent drug-loaded elements are held against the vessel wall by the stent structure. The predesigned pattern is fabricated to expand along a length of the stent to overcome strain.

As the stent is in an unexpanded condition, there is very little opening on the patterned sleeve. Upon expansion of the stent, the patterned sleeve has an opening that is less than the opening of the underlying stent structure in order to enable uniform drug delivery at the treatment site.

The patterned tubular sleeve portion of the drug-eluting stent delivery system also can be fabricated from a metallic material such as stainless steel, platinum, titanium, tantalum, nickel-titanium, cobalt-chromium, and alloys thereof.

In various embodiments, the patterned tubular sleeve portion may be fabricated with a plurality of depots and/or longitudinal channels to provide additional storage of therapeutic drugs loaded therein. In addition, the patterned tubular sleeve portion may be configured as a wave pattern, mesh pattern, or as a longitudinal slot pattern.

In another embodiment, the present invention provides for a drug-eluting stent delivery system for controlled release of therapeutic drugs and for delivery of the therapeutic drugs in localized drug therapy in a blood vessel. A pattern of struts are interconnected to form a first stent structure that contacts the walls of a body lumen to maintain the patency of the vessel, wherein a second stent structure, fabricated as a patterned thin metallic sheet having a polymer layer disposed thereon, is loaded with at least one therapeutic drug for the release thereof at a treatment site. The second stent structure is attached to at least a portion of an outside surface area of the stent structure. The second stent structure is not limited to a tubular form and can be wrapped around the first stent structure in a jelly roll configuration.

In a further embodiment, the present invention provides for a drug-eluting stent delivery system for controlled release of therapeutic drugs and for delivery of the therapeutic drugs in localized drug therapy in a blood vessel. A pattern of struts are interconnected to form a structure that contacts the walls of the body lumen to maintain the patency of the vessel. A plurality of individual filament strands are releasably attached to an outside surface of the stent structure in a spaced apart orientation and loaded with at least one therapeutic drug for the release thereof at a treatment site. The plurality of individual filament strands are positioned longitudinally across the outside surface of the stent structure in a circumferential manner.

In another embodiment, the plurality of individual filament strands are arranged longitudinally around an outside surface of a stent structure in a spaced apart orientation without being physically attached to the underlying stent structure. When the stent is in an expanded condition, the plurality of individual filament strands are held against the body lumen wall from the pressure of the stent.

The pattern of struts include a plurality of flexible cylindrical rings being expandable in a radial direction, each of the rings having a first delivery diameter and a second implanted diameter while aligned on a common longitudinal axis. At least one link of the stent is attached between adjacent rings to form the stent. The stent is formed at least in part of a metallic material such as stainless steel, platinum, titanium, tantalum, nickel-titanium, cobalt-chromium, and alloys thereof.

Various therapeutic drugs can be used in combination with the drug-eluting stent delivery system of the present invention including antiplatelets, anticoagulants, antifibrins, anti-inflammatories, antithrombins, and antiproliferatives. The plurality of individual filament strands can be fabricated using different therapeutic drug combinations for the release thereof at the treatment site. The drug-loaded filament strands each have a thickness in the range of about 0.001 to about 100.000 microns and a width in the range of about 0.001 to about 50.000 microns. Several drug-loadable polymers, such as PMMA, EVAL, PBMA, PGA, PLLA, copolymers and blends thereof, and nanotubes of carbon, can be used to fabricate the individual filament strands. Alternatively, the plurality of individual filament strands are fabricated from a porous metal having a polymeric drug release layer disposed thereon.

Each of the individual filament strands has a rectangular cross-section with a first side, a second side, a third side, and a fourth side. A barrier coating layer is disposed on the first, second, and third sides of each of the drug-loaded filament strands to enable drug elution along the fourth side at the treatment site facing the abluminal side of the artery. Alternatively, the plurality of individual filament strands can be configured to assume a different cross-sectional design such as circular, oval, triangular, trapezoidal, and tubular designs.

In other embodiments, the plurality of individual filament strands can be fabricated with a plurality of depots and/or longitudinal channels. The individual filament strands can be fabricated from either a micron-scale level or a nano-scale level to form microfilament strands or nanofilament strands, respectively.

In another embodiment, the present invention provides for a drug-eluting stent delivery system for controlled release of therapeutic drugs and for delivery of the therapeutic drugs in localized drug therapy in a blood vessel. A pattern of struts are interconnected to form a structure that contacts the walls of a body lumen to maintain the patency of the vessel. A polymeric sleeve, fabricated as a patterned tube, is loaded with at least one therapeutic drug for the release thereof at a treatment site, the polymeric sleeve being attached to at least a portion of an inside surface area of the stent structure for the treatment of the inner arterial region of the vessel.

In yet another embodiment, the present invention provides for a method of making a drug-eluting stent delivery system for controlled release of therapeutic drugs and for delivery of the therapeutic drugs in localized drug therapy in a blood vessel. The method includes providing a pattern of struts interconnected to form a structure that contacts the walls of a body lumen to maintain the patency of the vessel. A polymeric sleeve, fabricated as a patterned tube, is attached to at least a portion of an outer surface of the stent structure. The polymeric sleeve is loaded with at least one therapeutic drug for the release thereof at a treatment site.

In a further embodiment, the present invention provides for a method of making a drug-eluting stent delivery system for controlled release of therapeutic drugs and for delivery of the therapeutic drugs in localized drug therapy in a blood vessel. The method includes providing a pattern of struts interconnected to form a structure that contacts the walls of the body lumen to maintain the patency of the vessel. A plurality of individual filament strands are positioned longitudinally across an outside surface of the stent structure in a spaced apart orientation and attached thereto. The plurality of individual filament strands are loaded with at least one therapeutic drug for the release thereof at a treatment site.

In a still further embodiment, the present invention provides for a method of delivering a therapeutic drug within a body lumen. The method includes providing a stent having an outer surface and being in an unexpanded condition mounted on a stent delivery catheter. A prefabricated cover having a therapeutic drug selectively loaded into at least a portion of the cover is further provided. The cover may be releasably attached to the stent outer surface after the stent is mounted on the catheter assembly so that the drug is decoupled from the unexpanded stent. At least a portion of the cover is detached from the stent outer surface when the stent is expanded so that the drug loaded portion of the cover is pressed against the body lumen allowing the therapeutic drug to release into the body lumen.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

As shown in the drawings for purposes of illustration, the present invention is directed to a drug-eluting stent delivery system which includes a mechanical component and a local drug-eluting component, namely an intravascular stent and a prefabricated patterned sleeve for controlled release of therapeutic drugs and for delivery of the therapeutic drugs in localized drug therapy in a blood vessel. The present invention is also directed to an intravascular stent having a drug-eluting component in the form of a filament cover which includes a plurality of filament strands attached to an outer surface of the stent structure in a spaced apart orientation. Methods of making a drug-eluting stent delivery system having a drug-eluting component disposed in the form of a prefabricated patterned sleeve or filament cover for controlled release and delivery of therapeutic drugs in localized drug therapy in a blood vessel are also disclosed herein. Methods for delivering a therapeutic drug in localized drug therapy within a blood vessel are further disclosed herein.

Figures 1, 2, 3:
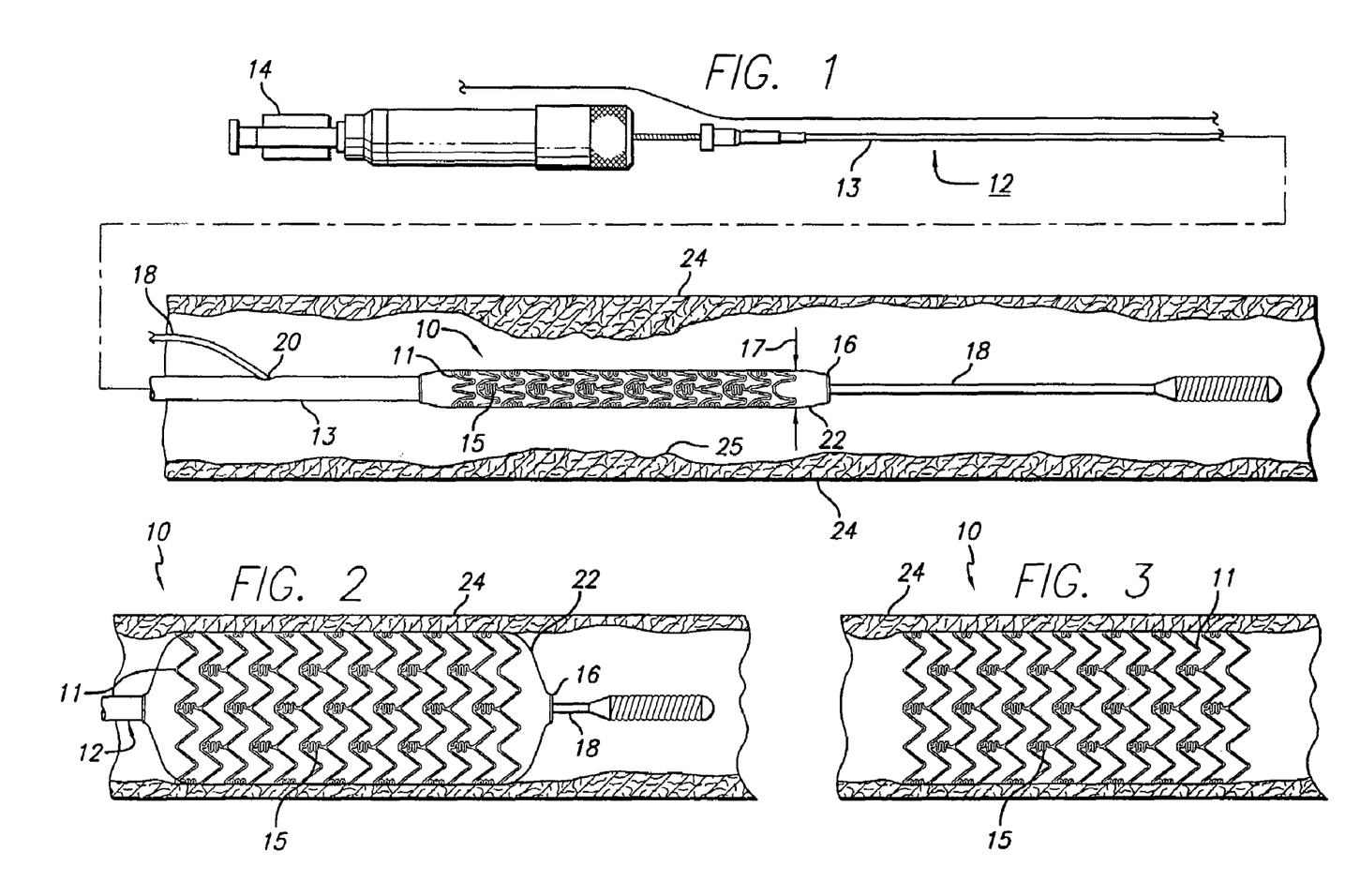
FIG. 1 is an elevational view, partially in section, of a stent embodying features of the invention which is mounted on a delivery catheter and disposed within a damaged artery.
FIG. 2 is an elevational view, partially in section, similar to that shown in FIG. 1 wherein the stent is expanded within a damaged artery.
FIG. 3 is an elevational view, partially in section, depicting the expanded stent within the artery after withdrawal of the delivery catheter.

Turning to the drawings, FIG. 1 depicts a metallic stent 10, incorporating features of the invention, mounted on a catheter assembly 12 which is used to deliver the stent and implant it in a body lumen, such as a coronary artery, carotid artery, peripheral artery, or other vessel or lumen within the body. The stent generally comprises a plurality of radially expandable cylindrical rings 11 disposed generally coaxially and interconnected by undulating links 15 disposed between adjacent cylindrical elements. The catheter assembly includes a catheter shaft 13 which has a proximal end 14 and a distal end 16. The catheter assembly is configured to advance through the patient's vascular system by advancing over a guide wire by any of the well known methods of an over the wire system (not shown) or a well known rapid exchange catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent 10 of the present invention is used to repair a diseased or damaged arterial wall which may include the plaque 25 as shown in FIG. 1, or a dissection, or a flap which are commonly found in the coronary arteries, carotid arteries, peripheral arteries and other vessels.

In a typical procedure to implant stent 10, the guide wire 18 is advanced through the patient's vascular system by well known methods so that the distal end of the guide wire is advanced past the plaque or diseased area 25. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 serves to hold open the artery 24 after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the closely spaced cylindrical elements at regular intervals provide uniform support for the wall of the artery, and consequently are well adapted to tack up and hold in place small flaps or dissections in the wall of the artery, as illustrated in FIGS. 2 and 3.

The stent patterns shown in FIGS. 1-3 are for illustration purposes only and can vary in size and shape to accommodate different vessels or body lumens. Further, the metallic stent 10 is of a type that can be used in accordance with the present invention. It can be appreciated that the present invention contemplates the use of virtually any stent design in conjunction with the drug-eluting component of the stent system. As such, the stent is not limited to solely a ring-link design as disclosed herein.

The drug-eluting stent delivery system of the present invention is applicable to all vascular stent applications in the body including coronary and peripheral arterial system. Further, the present invention can be used in the treatment of vulnerable plaque such as thin fibrous-capped atheromatic vulnerable lesions using desired drug and release kinetics with site specificity. In addition, the drug-eluting component of the stent system can be incorporated on all stent platforms for all sizes and lengths including a bifurcated stent structure to achieve uniform drug distribution along the entire vessel including the carina. It is also contemplated that the drug-eluting component of the present invention can be used for designing drug-eluting stent devices with thinner stent struts (i.e., thickness ranging between 5-100 microns) without compromising the structural integrity of the stent, deliverability and optimal drug elution.

The present invention overcomes all of the earlier mentioned limitations through a novel design that decouples the two major functional characteristics of the drug-eluting stent delivery system, namely the purely mechanical stent structure and the local drug-eluting component. Each component is independently designed and optimized for its functional characteristics and the optimal drug-eluting stent delivery system is conceived and assembled. The stent structure is optimally designed for expansion (i.e., allowable stress/strain, scaffolding, and radial strength), and the local drug-eluting component is optimally designed for controlled release of therapeutic drugs.

Figure 4A:
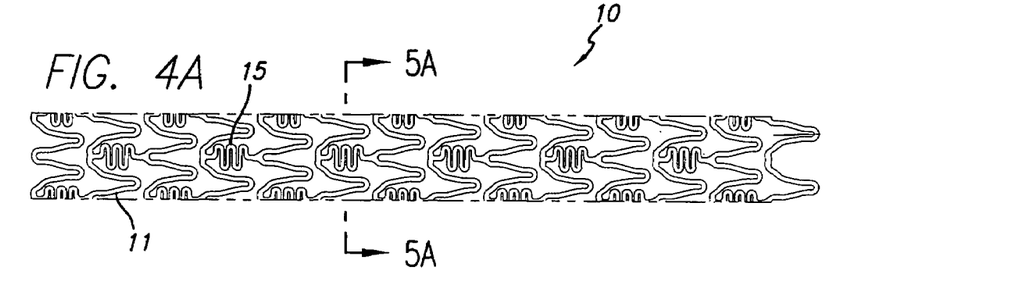
FIG. 4A is a plan view of a flattened stent of the invention which illustrates the pattern of the stent shown in FIGS. 1-3 in an unexpanded condition.

As shown in one embodiment, FIG. 4A is a plan view of a flattened stent of the drug-eluting stent delivery system which illustrates the pattern of the stent shown in FIGS. 1-3 in an unexpanded condition. The stent 10 is shown in a flattened condition so that the pattern can be clearly viewed, even though the stent is never in this form. The stent is typically formed from a tubular member, however, it can be formed from a flat sheet such as shown in FIG. 4A and rolled into a cylindrical configuration.

Figure 4B:
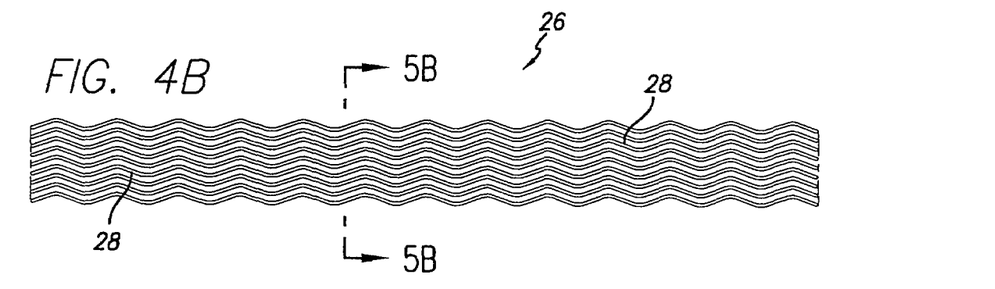
FIG. 4B is a plan view of a flattened drug-eluting component of the drug-eluting stent delivery system in accordance with the invention shown in the unexpanded condition.

FIG. 4B is a flattened, plan view of a prefabricated patterned polymeric sleeve 26 of the stent 10 in accordance with the invention shown in the unexpanded condition. In this embodiment, the stent having a polymeric sleeve for controlled release of therapeutic drugs and for delivery of the therapeutic drugs in localized drug therapy in a blood vessel includes a pattern of struts interconnected to form a structure that contacts the walls of a body lumen to maintain the patency of the vessel. The pattern of struts include a plurality of flexible cylindrical rings 11 (FIG. 4A) being expandable in a radial direction, each of the rings having a first delivery diameter and a second implanted diameter and being aligned on a common longitudinal axis 17. At least one link 15 (FIG. 4A) of the stent is attached between adjacent rings to form the stent.

With further reference to FIG. 4B, the drug-eluting polymeric sleeve 26 is prefabricated in the desired dimensions using conventional polymer processing methods known in the art, including extrusion, injection molding, slip casting or plasma polymerization using a mixture of the polymer, solvent and drug in liquid, semi-solid or solid form. The polymeric sleeve can be fabricated either as a patterned tube or a solid tube. When the polymeric sleeve is fabricated as a solid tube, the predesigned pattern can be attained by known methods in the art consisting of laser cutting or etching using the excimer or the avia solid-state laser without any post processing. The polymeric sleeve is fabricated from a predesigned pattern having individual drug-loaded elements 28 to form a desired local drug-elution profile. The predesigned pattern may be configured to include a plurality of struts (shown wavy in form, in FIG. 4B), the thickness of which depends on the particular polymer and the amount of drug loaded. Typically, the thickness of the struts ranges from about 10 nanometers to about 10 micrometers. The width of the struts is dependent on the drug properties and the desired degree of drug uniformity and drug uptake. Typically, the width of the struts ranges from about 100 nanometers to about 100 micrometers.

It should be appreciated that the intent of the prefabricated pattern on the polymeric sleeve is to enable the detachment of the sleeve 26 upon stent expansion (FIG. 6A) without undergoing stretching during balloon expansion of the stent 10 and achieve an optimally desired drug-elution profile. Accordingly, upon stent expansion, the polymeric sleeve decouples from the outer surface of the stent and the independent drug-loaded elements that are loaded into the decoupled sleeve are held against the vessel wall (not shown) by at least a portion of the patterned sleeve. The predesigned pattern can be fabricated so that it expands along a length of the stent if needed to overcome strain during expansion. Accordingly, due to the pattern of the polymeric sleeve, the polymeric sleeve is not distorted upon expansion. Moreover, with regard to longitudinal distortion, the polymeric sleeve may be attached at selected locations or completely detached (as set forth below) from the stent structure to enable uniform deployment based on the type of delivery system used. For example, the drug-eluting stent delivery system may be deployed using a balloon without folds. The sleeve may be attached to the stent using conventional metal-polymer or polymer-polymer adhesion techniques known in the art. The drug-loaded polymeric sleeve has a thickness in the range of about 0.001 microns to about 100.000 microns.

In keeping with the present invention, the drug-loaded sleeve may encompass an outer surface of the stent without being physically attached thereto. With such type of configuration, upon expansion of the stent, the independent drug-loaded elements loaded into the sleeve portion are decoupled from the outer surface of the stent so that the independent drug-loaded elements are held against the vessel wall from the pressure of the underlying stent. It is further contemplated that the drug-loaded sleeve, upon expansion of the stent, completely releases from the outer surface of the stent while being held against the vessel wall from the pressure of the underlying stent.

Figure 4C:
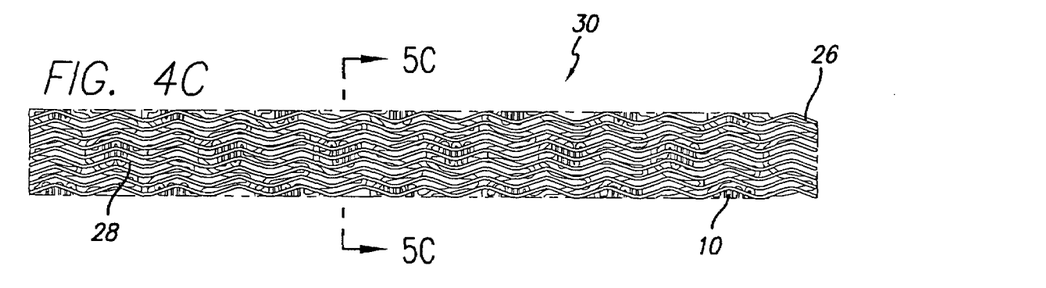
FIG. 4C is a plan view of the drug-eluting stent delivery system in accordance with the invention shown in the unexpanded condition.

FIG. 4C is a plan view of the drug-eluting stent delivery system 30, which includes a stent 10 with the drug-eluting component or polymeric sleeve 26 disposed thereon in accordance with the invention shown in the unexpanded condition.

Figure 5A:
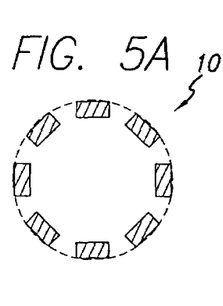
FIG. 5A is a transverse, cross-sectional view of the drug-eluting stent delivery system shown in FIG. 4A in the unexpanded condition.
Figure 5B:
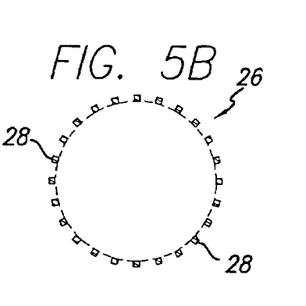
FIG. 5B is a transverse, cross-sectional view of the drug-eluting component of the drug-eluting stent delivery system shown in FIG. 4B in the unexpanded condition.
Figure 5C:
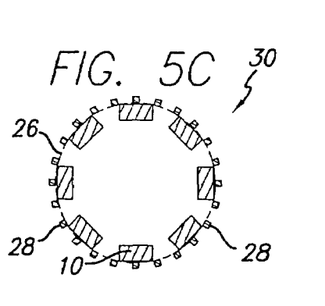
FIG. 5C is a transverse, cross-sectional view of the drug-eluting stent delivery system shown in FIG. 4C in the unexpanded condition.

FIGS. 5A-C depict various transverse, cross-sectional views of the two separate components of the drug-eluting stent delivery system 30, namely the mechanical stent structure 10 and the drug-eluting component or drug-loaded polymeric sleeve 26, and one of the complete present invention drug-eluting stent delivery system while in an unexpanded condition. More specifically, FIG. 5A is a transverse, cross-sectional view of the stent in FIG. 4A shown in the unexpanded condition. FIG. 5B is a transverse, cross-sectional view of the drug-eluting component of the stent in FIG. 4B shown in the unexpanded condition. FIG. 5C is a transverse, cross-sectional view of the stent with the drug-eluting component disposed thereon in FIG. 4C shown in the unexpanded condition.

Figures 6A, 6B, 7A, 7B:
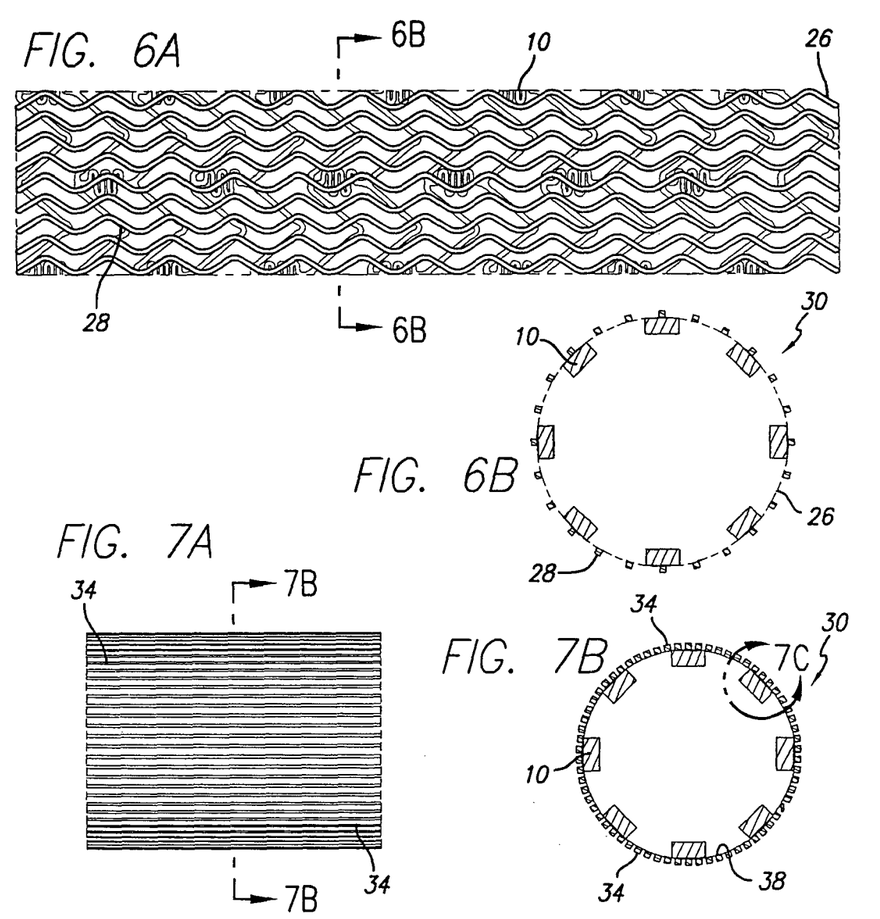
FIG. 6A is a plan view of the drug-eluting stent delivery system in accordance with the invention shown in the expanded condition.
FIG. 6B is a transverse, cross-sectional view of the drug-eluting stent delivery system of FIG. 6A shown in the expanded condition.
FIG. 7A is a plan view of an alternative embodiment of the invention in an expanded condition depicting a plurality of individual filament strands for holding the therapeutic drug prior to being released.
FIG. 7B is a transverse, cross-sectional view of the alternative embodiment depicting a stent with the plurality of individual filament strands attached thereto in the expanded condition.

FIG. 6A illustrates a plan view of the stent 10 with the drug-loaded polymeric sleeve 26 disposed thereon in accordance with the invention shown in the expanded condition. The present invention contemplates that the drug-loaded polymeric sleeve can have at least one additional layer of polymer material as a barrier layer to control elution of the therapeutic drug at the treatment site. Multiple layers of polymer material disposed on the polymeric sleeve provide further control of the elution of the therapeutic drug at the treatment site. It should be further recognized that the polymeric sleeve can optionally include multiple layers of the therapeutic drug disposed thereon. Accordingly, each of the layers of therapeutic drug can comprise a different therapeutic drug with varying release rates or a mixture of different therapeutic drugs. The outermost layer has a polymeric barrier coat layer to further control elution of the therapeutic drug. FIG. 6B illustrates a transverse, cross-sectional view of the drug-eluting stent delivery system 30 of FIG. 6A in the expanded condition. In this embodiment, the complete polymeric sleeve also may be coated with a top coat or barrier layer along the inner surface to prevent washout of the drug and increase efficiency of drug uptake into the artery.

It is further contemplated by the present invention that the drug-loaded sleeve portion of the drug-eluting stent delivery system may be fabricated from other materials, such as metals, aside from exclusively polymers.

The patterned polymeric sleeve portion is configured to have an opening in the range from about 0.1 mm$^2$ up to about 4.0 mm$^2$ in area or about 0.3 mm up to about 2.0 mm in length when the stent is in an expanded condition. Regarding the stiffness and resistance of the polymeric sleeve portion to expansion, the sleeve negligibly adds to the stiffness of the underling device in terms of requiring additional expansion force or causing the stent to recoil. Typically, the elastic modulus or stiffness of materials that form the stent structure are in the range of about 50 gigapascals to about 300 gigapascals. The stiffness of the sleeve material is about 10 to about 1000 times lower, in the range from about 0.05 gigapascals to about 30.00 gigapascals. The polymeric sleeve portion has a stiffness of about 100 to about 1000 times lower compared to the material, in the range of about 0.05 megapascals to about 30.00 megaspascals.

Figure 7C:
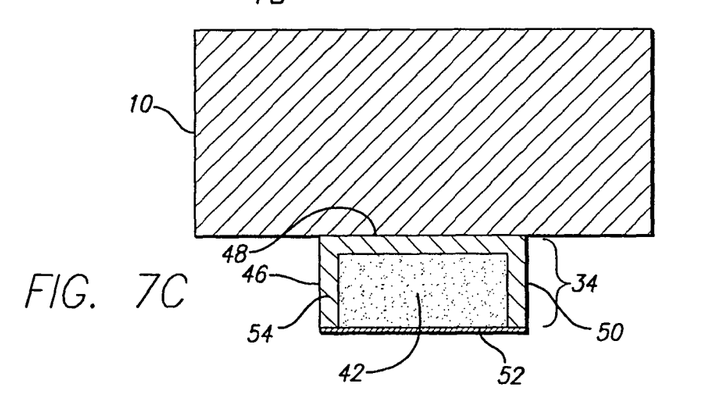
FIG. 7C is an enlarged, transverse, cross-sectional view of a section shown in FIG. 7B in the expanded condition.

In another embodiment shown in FIGS. 7A-C, the present invention accordingly provides for a drug-eluting stent delivery system 30 having a drug-eluting component 34 for controlled release of therapeutic drugs and for delivery of the therapeutic drugs in localized drug therapy in a blood vessel. A pattern of struts are interconnected to form a structure 10 that expands into the walls of the body lumen to maintain the patency of the vessel. The pattern of struts include a plurality of flexible cylindrical rings 11 being expandable in a radial direction, each of the rings having a first delivery diameter and a second implanted diameter and being aligned on a common longitudinal axis 17. At least one link 15 of the stent is attached between adjacent rings to form the stent. A plurality of individual filament strands 34 are attached to an outer surface 38 of the stent structure in a spaced apart orientation, wherein the plurality of filament strands are each loaded with at least one therapeutic drug 42 for the release thereof at a treatment site. The plurality of individual filament strands are each positioned longitudinally across the outside surface of the stent structure in a circumferential manner.

FIG. 7A illustrates a typical arrangement of the individual filament strands 34 prior to their attachment to an outer surface of the stent structure in a spaced apart orientation. The filament strands are pre-loaded with at least one therapeutic drug for the eventual release thereof at the treatment site. It should be appreciated that the present invention contemplates the use of several different types of therapeutic drugs and drug cocktail combinations by incorporating different filament strands fabricated using different therapeutic drugs and therapeutic drugs with polymers for the eventual release thereof at the treatment site. The drug-loaded filament strands have dimensions of about 0.001 to about 100.000 microns in thickness and about 0.001 to about 50.000 microns in width. These filament strands can be fabricated from the micron to nanoscale level as wires or tubes from polymers and metals.

FIG. 7B is a transverse, cross-sectional view of one embodiment of the invention, depicting a stent 10 with the plurality of individual filament strands 34 attached thereto in the expanded condition. The plurality of individual filament strands can be attached to the outer surface 38 of the stent by utilizing one of the techniques known in the art including metal-polymer and polymer-polymer bonding technologies (i.e., adhesives). The drug-loaded filament strands can be designed to expand along the length of the stent to overcome strain as a result of expansion if necessary. Due to the unique design of the drug-loaded filament strands, the filament strands are not distorted upon expansion.

Referring to FIG. 7C, each individual drug-loaded filament strand 34 has a rectangular cross-section 44 with a first side 46, second side 48, third side 50, and a fourth side 52. A polymeric barrier coating layer 54 is disposed on the first through third sides of each of the drug-loaded filament strands to enable drug elution along the fourth side at the treatment site. This layered construct increases the efficiency of drug transfer into the artery with minimal washout of the therapeutic drug. Accordingly, a lesser amount of drug 42 and fewer polymers are needed to deliver the appropriate therapeutic dose of drug into the artery. The local drug release rate at specific sites along the length and diameter of the stent can be varied by incorporating filament strands with different drug release rates into the drug-eluting stent delivery system. Further, the drug-loaded filament strands can have multiple layers of polymer to control drug elution kinetics, such as a top coat barrier layer to control or prevent drug release. Optionally, each filament strand can comprise multiple layers for loading with different therapeutic drugs or a mixture of different therapeutic drugs. The outermost layer has a polymeric barrier coat layer to further control elution of the therapeutic drug.

Other cross-sectional designs may be utilized and optimized to achieve the desired drug elution kinetics of the present invention. Examples of alternative cross-sectional designs that may be employed for use with the drug-eluting stent delivery system include circular, oval, triangular, trapezoidal, and tubular designs. The plurality of individual filament strands can be alternatively fabricated from a porous metal having a polymeric drug release layer disposed thereon.

It should be appreciated that the drug-loaded filament strands 34 can be used in combination with the prepatterned polymeric sleeve 26 embodiment. In such an arrangement, each individual drug-loaded filament strand is placed longitudinally along the outer surface of the polymeric sleeve and attached thereto by polymer-polymer bonding or other similar methods (i.e. adhesives) known in the art. A barrier coating layer 54 is disposed on the first through third sides of each of the drug-loaded filament strands to enable drug elution along the fourth side at the treatment site as shown in FIG. 7C.

Figures 8A, 8B:
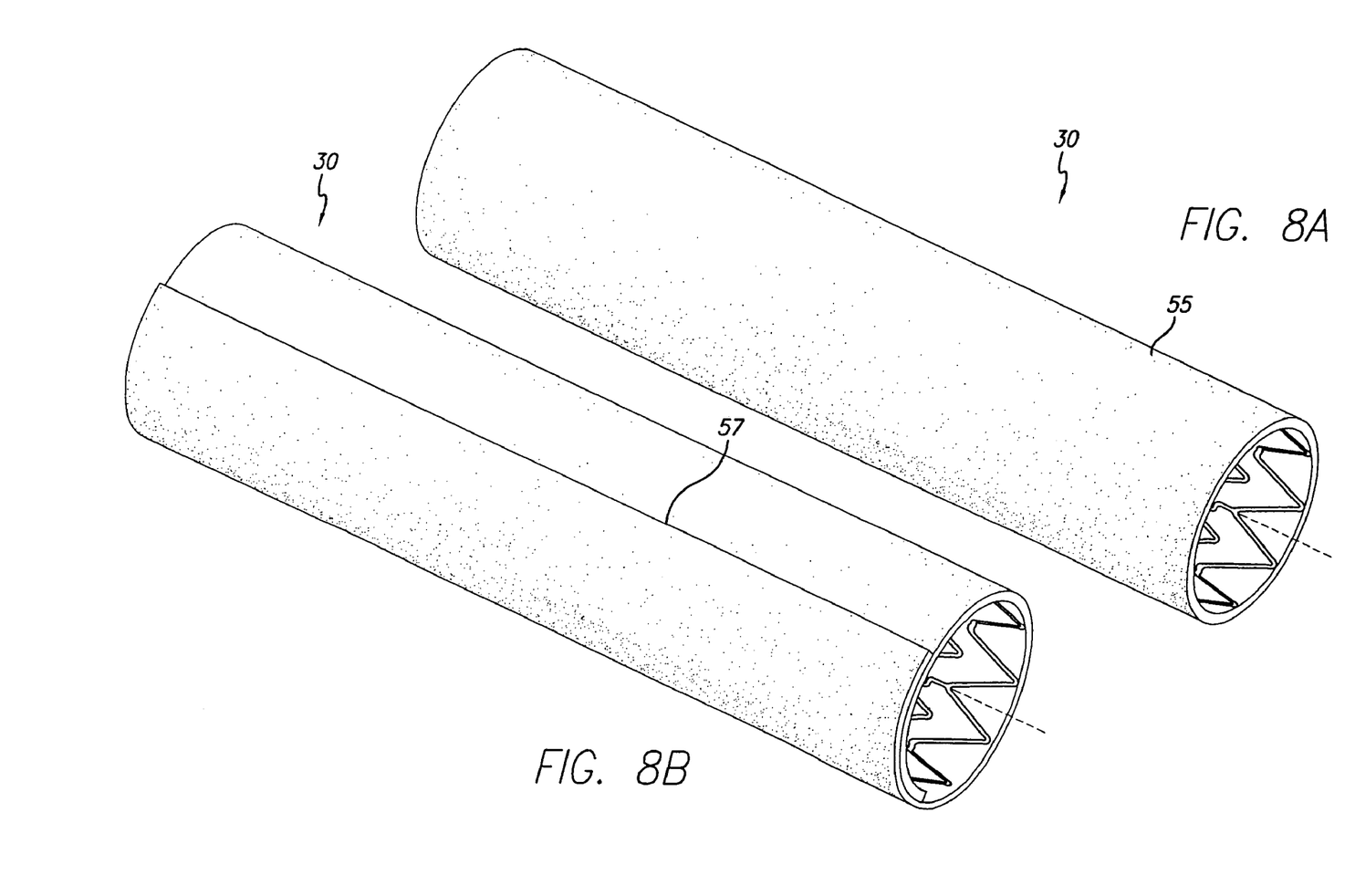
FIG. 8A is a plan view of an alternative embodiment of the invention depicting a stent structure fabricated as a thin metallic sheet attached to at least a portion of an outer surface of an underlying stent structure.
FIG. 8B is a plan view of an alternative embodiment of the invention depicting a thin metallic sheet attached to an outer surface of an underlying stent structure in a jelly roll configuration.

In another embodiment, the present invention provides for a drug-eluting stent delivery system for controlled release of therapeutic drugs and for delivery of the therapeutic drugs in localized drug therapy in a blood vessel. A pattern of struts are interconnected to form a first stent structure that contacts the walls of a vessel to maintain the patency of the vessel. As shown in FIG. 8A, a second stent structure 55 in tubular form, fabricated as a patterned thin metallic sheet having a polymer layer disposed thereon, is loaded with at least one therapeutic drug for the release thereof at a treatment site, the second stent structure being attached to at least a portion of an outer surface of the first stent structure 10. It should be appreciated that the second stent structure is not limited to a tubular form, and can be fabricated as a thin metallic sheet attached to the outer surface of the first stent structure by being wrapped around the first stent structure in a jelly roll configuration 57 (FIG. 8B). Various mechanisms for attaching the second stent structure to the outer surface of the first stent structure are known in the art and contemplated for use with the present invention. Examples of such mechanisms for attachment include metal-polymer and polymer-polymer bonding technologies, such as by adhesives, laser bonding, and other similar methods.

Figure 9A:
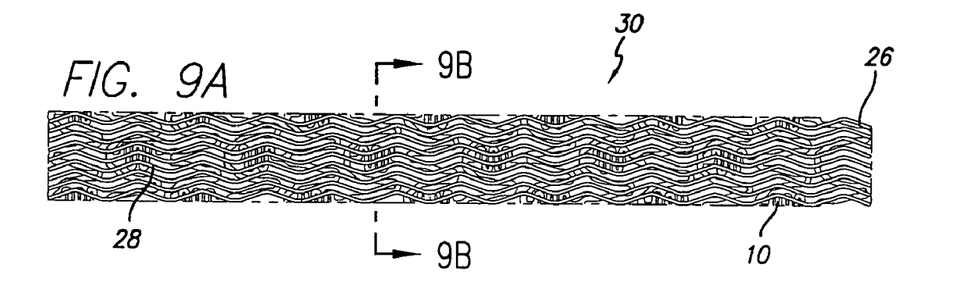
FIG. 9A is a plan view of an alternative embodiment of the invention depicting a polymeric sleeve attached to at least a portion of an inner surface of the stent.
Figure 9B:
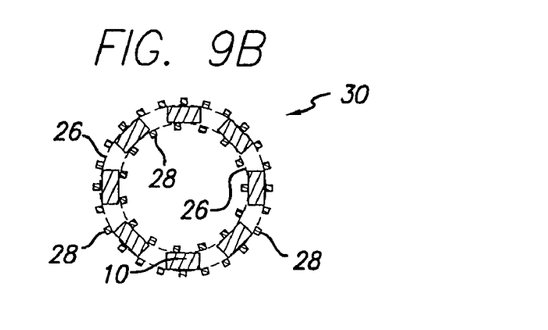
FIG. 9B is a transverse, cross-sectional view of the alternative embodiment of the invention shown in FIG. 9A in the unexpanded condition.

In yet another embodiment, the present invention provides for a drug-eluting stent delivery system for controlled release of therapeutic drugs and for delivery of the therapeutic drugs in localized drug therapy in a blood vessel. A pattern of struts are interconnected to form a structure that expands into the walls of a vessel to maintain the patency of the vessel, wherein a polymeric sleeve, fabricated as a prepatterned tube, is loaded with at least one therapeutic drug for the release thereof at a treatment site. As shown in FIGS. 9A-9B, the polymeric sleeve 26 can be attached to at least a portion of an inner surface of the stent structure 10 to provide for appropriate treatment of the inner arterial region through release of the therapeutic drug in that region of the vessel where the stent is placed.

Figure 10:
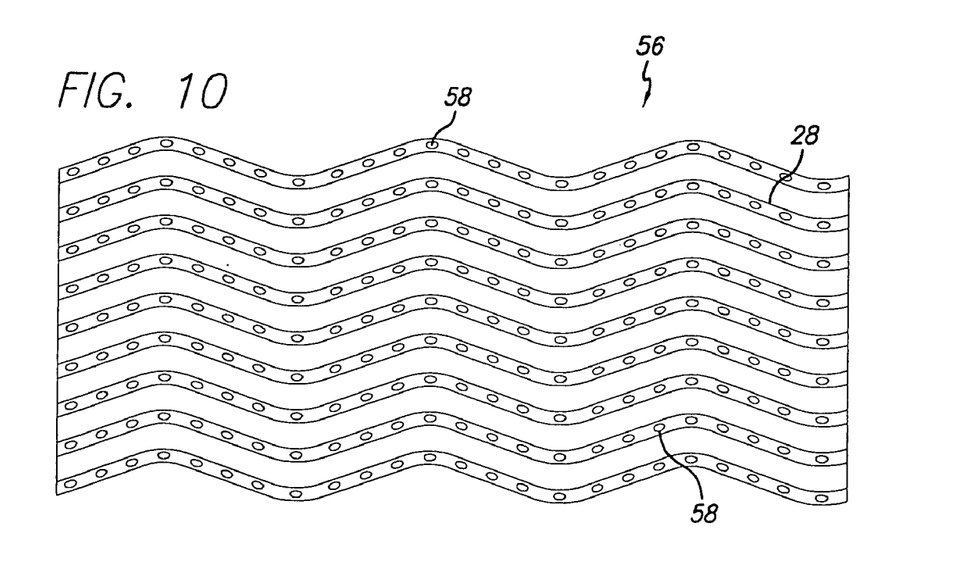
FIG. 10 is an enlarged plan view of an alternative embodiment of the invention depicting a prepatterned tubular sleeve portion fabricated from a metallic material with a plurality of depots molded therein.
Figure 11:
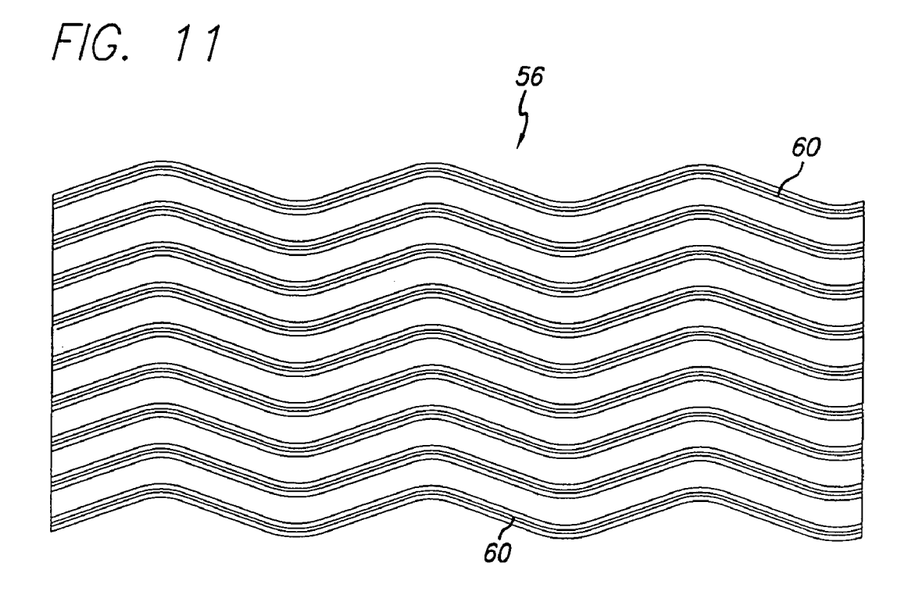
FIG. 11 is an enlarged plan view of an alternative embodiment of the invention depicting the prepatterned tubular sleeve portion fabricated from a metallic material with a plurality of longitudinal channels molded therein.
Figure 12:
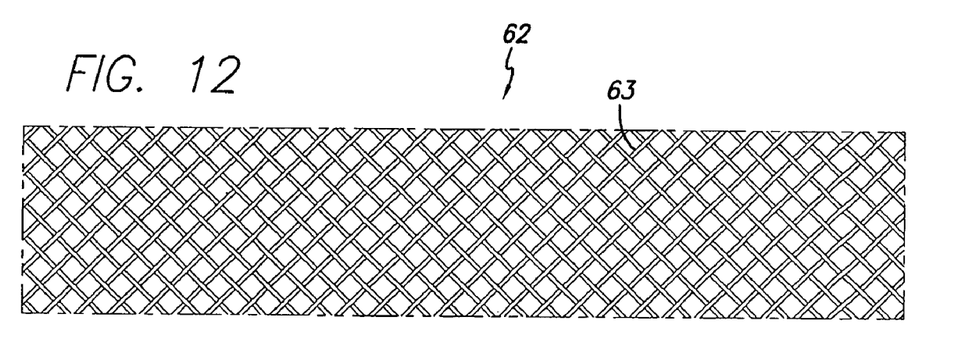
FIG. 12 is an enlarged plan view of an alternative embodiment of the invention depicting the prepatterned tubular sleeve portion configured as a braided mesh pattern.
Figure 13:
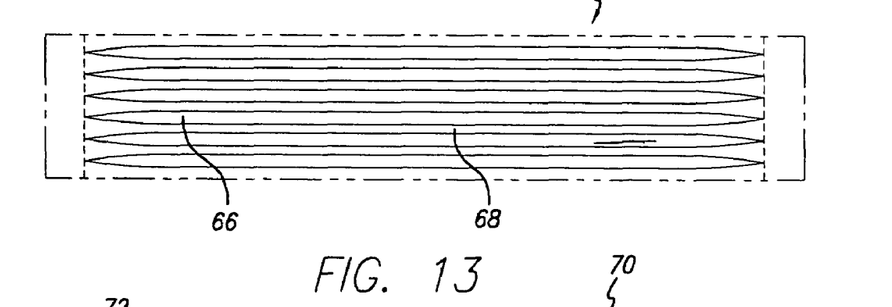
FIG. 13 is a plan view of an alternative embodiment of the invention depicting the prepatterned tubular sleeve portion configured as a plurality of longitudinal slots.

Depending on the desired nature of local drug elution and drug uptake into the artery, a variety of different patterns can be etched or cut into the particular material that forms the sleeve. As earlier disclosed in FIG. 4B, the sleeve portion may assume a pattern that is wavy in form. Exemplary of such additional types of patterns include, but are not limited to, those set forth in FIGS. 10-13. Specifically, in one embodiment shown in FIG. 10, a plurality of depots 58 can be injection molded into the sleeve portion 56 according to such processes known in the art. In another embodiment shown in FIG. 11, a plurality of longitudinal channels 60 can be injection molded into the sleeve portion 56 according to such processes known in the art. It is further contemplated that a combination of depots and channels can be injection molded into the sleeve. The depots and channels provide additional space within the sleeve portion for storage of therapeutic drugs. Alternatively, as shown in FIG. 12, the sleeve portion 62 may assume a pattern that is of a braided mesh 63 type in form. In FIG. 13, the sleeve portion 64 may include a longitudinal slot pattern 66 formed therein such that upon expansion of the sleeve each slot assumes a diamond-shaped configuration. Further, with the expansion of the sleeve portion, each drug-loaded element 68 expands outward at the perforated edges 67 of the sleeve and into the vessel wall.

Figure 14:
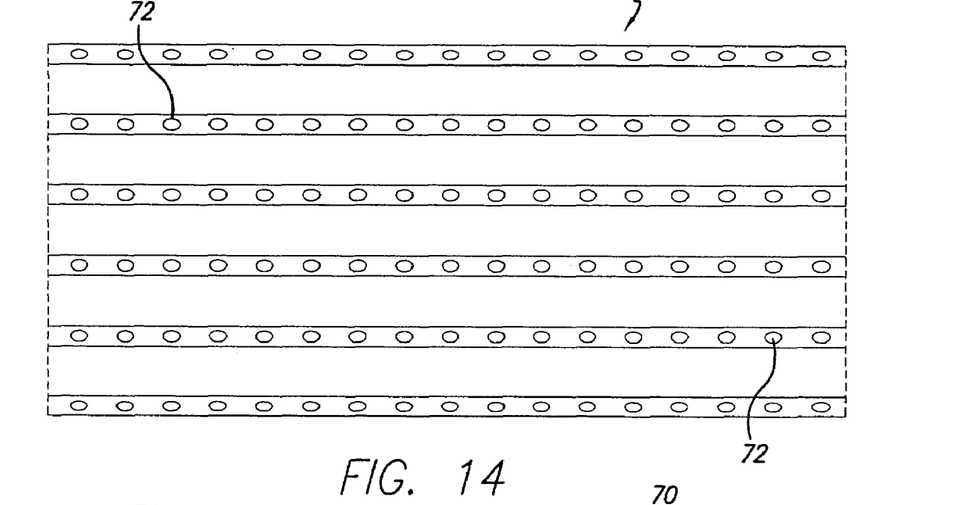
FIG. 14 is an enlarged plan view of an alternative embodiment of the invention depicting a filament cover having a plurality of depots molded therein.
Figure 15:
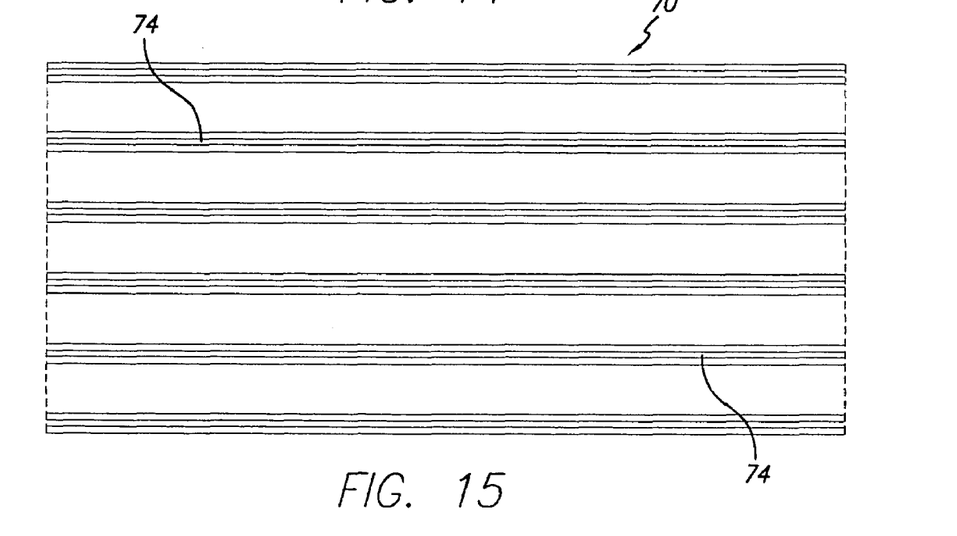
FIG. 15 is an enlarged plan view of an alternative embodiment of the invention depicting a filament cover having a plurality of longitudinal channels molded therein.
Figure 16A:
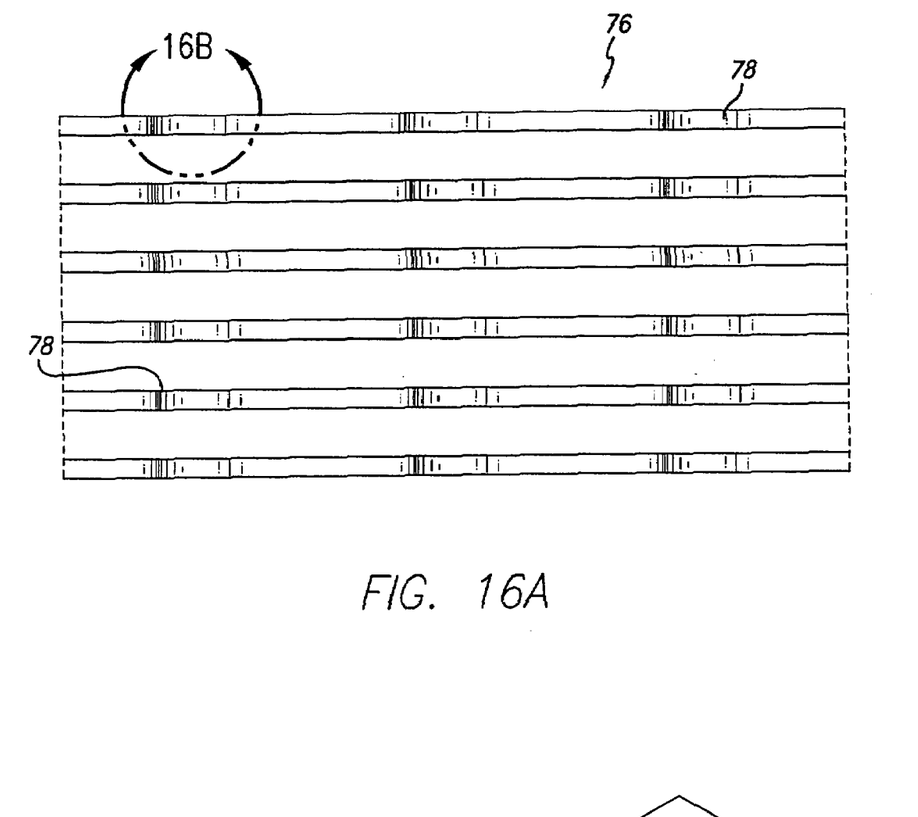
FIG. 16A is a plan view of an alternative embodiment of the invention depicting a filament cover having a plurality of undulations formed therein.
Figure 16B:
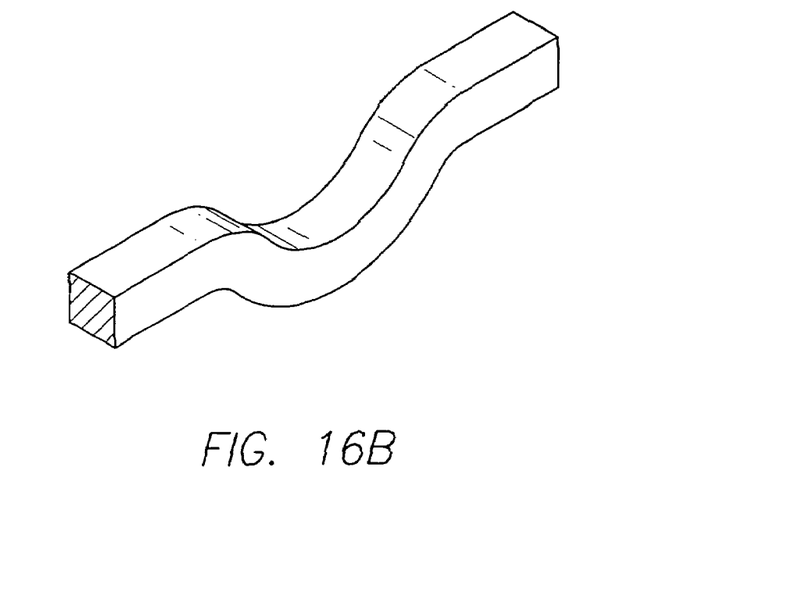
FIG. 16B is an enlarged view of an undulation formed within an individual filament strand.

Similarly, a variety of different patterns can be etched or cut into the particular material that forms each individual filament strand of the filament cover. Exemplary of such additional types of patterns include, but are not limited to, those set forth in FIGS. 14-16. In one embodiment shown in FIG. 14, a plurality of depots 72 can be injection molded into the filament cover 70 in accordance with such processes known in the art. In another embodiment shown in FIG. 15, a plurality of longitudinal channels 74 can be injection molded into the filament cover 70 in accordance with such processes known in the art. Alternatively, a combination of depots and channels can be injection molded into the sleeve. As shown in FIG. 16A, each individual filament strand of the filament cover 76 may include a plurality of undulations 78 formed therein. FIG. 16B illustrates an enlarged view of an undulation formed within an individual filament strand.

Examples of various metals or alloys used in forming the mechanical stent structure of the present invention drug-eluting stent delivery system include stainless steel, platinum, titanium, tantalum, nickel-titanium, cobalt-chromium, and alloys thereof. The stent can also be formed of a polymeric material such as PMMA, PGA or PLLA. Examples of various polymers used in forming the local drug-eluting component of the drug-eluting stent delivery system for all of the embodiments include PMMA, EVAL, PBMA, biodegradable polymers (i.e., PGA and PLLA), copolymers and blends thereof, and nanotubes of carbon. As set forth above, the local drug-eluting component may be alternatively fabricated from various metals or alloys, including stainless steel, platinum, titanium, tantalum, nickel-titanium, cobalt-chromium, and alloys thereof.

Examples of therapeutic drugs or pharmacologic compounds that may be loaded into the prefabricated patterned, polymeric sleeve or individual filament strands and delivered to the target site in the vasculature include taxol, aspirin, prostaglandins, and the like. Various therapeutic agents such as antithrombogenic or antiproliferative drugs are used to further control local thrombosis. Examples of therapeutic agents or drugs that are suitable for use in accordance with the present invention include sirolimus, everolimus, actinomycin D (ActD), taxol, paclitaxel, or derivatives and analogs thereof. Examples of agents include other antiproliferative substances as well as antineoplastic, anti-inflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents include antiplatelets, anticoagulants, antifibrins, antiinflammatories, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents is known in the art. The calculation of dosages, dosage rates and appropriate duration of treatment are previously known in the art. Furthermore, the therapeutic drugs or agents are loaded at desired concentration levels per methods well known in the art to render the device ready for implantation. It is contemplated that the prefabricated patterned sleeve portion of the present invention may have a drug loading capacity in the range from about 0.1 micrograms to about 100 milligrams of therapeutic drug or agent.

In use, the stent is deployed using conventional techniques. Once in position, the therapeutic drug gradually diffuses into adjacent tissue at a rate dictated by the parameters associated with the polymer coat layer. The total dosage that is delivered is of course limited by the total amount of the therapeutic drug that had been loaded within the polymer sleeve or within each individual strand of the plurality of microfilaments. The therapeutic drug is selected to treat the deployment site and/or locations downstream thereof. For example, deployment in the carotid artery will serve to deliver such therapeutic drug to the brain.

The present invention also provides a method for delivering therapeutic drugs within a body lumen. In one embodiment, the method includes providing a stent 10 having an outer surface 38 with the stent in an unexpanded condition mounted on a stent delivery catheter 12. A therapeutic drug is selectively loaded into at least a portion of a prefabricated cover 26. The prefabricated cover is releasably attached to the stent outer surface after the stent is mounted on the catheter assembly so that the drug is decoupled from the unexpanded stent. At least a portion of the cover is detached from the stent outer surface when the stent is expanded so that the drug loaded portion of the cover is pressed against the body lumen allowing the therapeutic drug to release into the body lumen.

The present invention further provides for various methods of making a drug-eluting stent delivery system 30 for controlled release of therapeutic drugs and for delivery of the therapeutic drugs in localized drug therapy in a blood vessel. In one embodiment, the method includes providing a pattern of struts interconnected to form a structure 10 that contacts the walls of a body lumen to maintain the patency of the vessel. A polymeric sleeve 26, fabricated as a patterned tube, is attached to at least a portion of an outer surface 38 of the stent structure. Fabrication of the polymeric sleeve may be accomplished through using a variety of different techniques known in the art which include extrusion, laser cutting, plasma polymerization, slip casting, injection molding and similar techniques. The pattern of the polymeric tube may assume any desirable pattern which works to achieve an appropriate local drug-elution profile.

In an alternative embodiment, the local drug-eluting component 34 includes a plurality of individual filament strands which are longitudinally positioned across an outer surface 38 of a stent structure 10 in a spaced apart orientation and attached thereto. The plurality of individual filament strands are loaded with at least one therapeutic drug 42 for the release thereof at a treatment site.

The drug-loaded sleeve or the drug-loaded filament strands can be processed directly by methods known in the art, such as by extrusion or plasma polymerization. The drug-loaded, prefabricated patterned polymeric sleeve or the individual drug-loaded filament strands are preferably attached to the stent structure in the final stages of fabricating the drug-eluting stent delivery system, after the stent is crimped and securely attached to the balloon using current technology. The polymeric sleeves or filament strands of appropriate length are attached to the outer surface of the stent on the delivery system using various metal-polymer and polymer-polymer bonding technologies, such as adhesives.

The aforedescribed illustrative stent 10 of the present invention and similar stent structures can be made in many ways. One method of making the stent rings 11 is to cut a thin-walled tubular member, such as stainless steel tubing to remove portions of the tubing in the desired pattern for the stent, leaving relatively untouched the portions of the metallic tubing which are to form the rings. In accordance with the invention, it is preferred to cut the tubing in the desired pattern using a machine-controlled laser which process is well known in the art.

After laser cutting, the stent rings are preferably electrochemically polished in an acidic aqueous solution such as a solution of ELECTRO-GLO #300, sold by the ELECTRO-GLO Co., Inc. in Chicago, Ill., which is a mixture of sulfuric acid, carboxylic acids, phosphates, corrosion inhibitors and a biodegradable surface active agent. The bath temperature is maintained at about 110-135° F. and the current density is about 0.4 to about 1.5 amps per square inch. Cathode to anode area should be at least about two to one.

The foregoing laser cutting process to form the cylindrical rings 11 can be used with metals other than stainless steel including cobalt-chromium, titanium, tantalum, platinum, nickel-titanium, and alloys thereof, and other biocompatible metals suitable for use in humans, and typically used for intravascular stents. Further, while the formation of the cylindrical rings is described in detail, other processes of forming the rings are possible and are known in the art, such as by using chemical etching, electronic discharge machining, stamping, and other processes.

While the invention has been illustrated and described herein, in terms of its use as an intravascular stent, it will be apparent to those skilled in the art that the stent can be used in other body lumens. Further, particular sizes and dimensions, materials used, and the like have been described herein and are provided as examples only. Likewise, the invention is not limited to any particular method of forming the underlying medical device structure. Other modifications and improvements may be made without departing from the scope of the invention. Accordingly, it is not intended that the invention be limited, except as by the appended claims.

I claim:

1. A sleeve loaded with at least one therapeutic drug for the eventual release thereof at a treatment site within a body lumen, comprising:
   a prefabricated patterned tubular sleeve portion having independent drug-loaded elements, the patterned tubular sleeve portion being releasably attached to an outer surface of a stent structure in an unexpanded condition, at least a portion of the patterned tubular sleeve portion being decoupled from the outer surface of the stent structure when the stent structure is in an expanded condition so that the independent drug-loaded elements are held against the body lumen by at least a portion of the patterned tubular sleeve portion, wherein the sleeve is not stretched when the stent structure expands from the unexpanded condition to the expanded condition, and
   wherein the patterned tubular sleeve portion is configured as a wave pattern.

2. A sleeve loaded with at least one therapeutic drug for the eventual release thereof at a treatment site within a body lumen, comprising:
   a prefabricated patterned tubular sleeve portion having independent drug-loaded elements, the patterned tubular sleeve portion being releasably attached to an outer surface of a stent structure in an unexpanded condition, the stent structure having a longitudinal axis and a transverse cross-section defining a circumference, at least a portion of the patterned tubular sleeve portion being decoupled from the outer surface of the stent structure when the stent structure is in an expanded condition so that the independent drug-loaded elements are held against the body lumen by at least a portion of the patterned tubular sleeve portion, wherein the independent drug-loaded elements are positioned longitudinally across the outer surface of the stent structure and spaced apart from each other over the circumference, and wherein the patterned tubular sleeve portion is configured as a wave pattern.

3. The sleeve of claim 2, wherein the patterned tubular sleeve portion is fabricated from a polymeric material.

4. The sleeve of claim 2, wherein the patterned tubular sleeve portion is fabricated from a metallic material.

5. The sleeve of claim 2, wherein the patterned tubular sleeve portion includes a plurality of depots.

6. The sleeve of claim 2, wherein the patterned tubular sleeve portion includes a plurality of longitudinal channels.

7. The sleeve of claim 2, wherein upon expansion of the stent structure, the patterned tubular sleeve portion completely releases from the outer surface of the stent structure.

8. The sleeve of claim 2, wherein upon expansion of the stent structure, the patterned tubular sleeve portion has an opening in the range from about 0.1 mm² to about 4.0 mm² in area.

9. The sleeve of claim 2, wherein upon expansion of the stent structure, the patterned tubular sleeve portion has an opening in the range from about 0.3 mm to about 2.0 mm in length.

10. The sleeve of claim 2, wherein the patterned tubular sleeve portion includes a pattern of struts interconnected to form the sleeve for contacting at least a portion of the walls of the body lumen.

11. The sleeve of claim 10, wherein the struts have a radial thickness in the range form about 10 nanometers to about 10 micrometers.

12. The sleeve of claim 10, wherein the struts have a width in the range from about 100 nanometers to about 100 micrometers.

13. The sleeve of claim 2, wherein the patterned tubular sleeve portion has an elastic modulus in the range from about 0.05 megapascals to about 30.00 megapascals.

14. The sleeve of claim 2, wherein the patterned tubular sleeve portion has a drug loading capacity in the range from about 0.1 micrograms to about 100 milligrams of therapeutic drug or agent.

15. The sleeve of claim 2, wherein each of the independent drug-loaded elements is releasably adhered to the outer surface of the stent structure in the unexpanded condition.

16. The sleeve of claim 2, wherein the independent drug-loaded elements extend in a circumferential direction about the circumference of the stent structure and extend in a longitudinal direction to a greater extent than in the circumferential direction.

17. The sleeve of claim 2, wherein after the stent structure expands from the unexpanded condition to the expanded condition, the independent drug-loaded elements are separated by gaps extending in a circumferential direction about the circumference of the stent structure and extending in a longitudinal direction to a greater extent than in the circumferential direction.

18. The sleeve of claim 2, wherein the independent drug-loaded elements are not connected to each other after the stent structure expands from the unexpanded condition to the expanded condition.

19. The sleeve of claim 2, wherein the stent structure includes a plurality of radially expandable cylindrical rings and each of the independent drug-loaded elements are positioned longitudinally across the plurality of cylindrical rings.

20. The sleeve of claim 19, wherein at least one of the plurality of radially expandable cylindrical rings supports each of the independent drug-loaded elements.

* * * * *

UNITED STATES PATENT AND TRADEMARK OFFICE
CERTIFICATE OF CORRECTION

PATENT NO. : 7,435,255 B1  Page 1 of 1
APPLICATION NO. : 10/668077
DATED : October 14, 2008
INVENTOR(S) : K. T. Venkateswara Rao It is certified that error appears in the above-identified patent and that said Letters Patent is hereby corrected as shown below:

On the Title page, above the Inventor information change the title to read:

--(54) DRUG-ELUTING STENT AND METHOD OF MAKING SAME--.

On the first page, below the Inventor information change the assignee to read:

--(73)    Advanced Cardiovascular Systems, Inc., Santa Clara, CA (US)--.

On page 11, beginning of column 1, change the title to read:

--DRUG-ELUTING STENT AND METHOD OF MAKING SAME--.

Signed and Sealed this

Eighth Day of June, 2010

David J. Kappos
*Director of the United States Patent and Trademark Office*